United States Patent
Nishigaki

(10) Patent No.: US 9,575,083 B2
(45) Date of Patent: Feb. 21, 2017

(54) AUTOMATIC ANALYSIS APPARATUS

(71) Applicant: HITACHI HIGH-TECHNOLOGIES CORPORATION, Tokyo (JP)

(72) Inventor: Kenichi Nishigaki, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 14/762,922

(22) PCT Filed: Jan. 22, 2014

(86) PCT No.: PCT/JP2014/051172
§ 371 (c)(1),
(2) Date: Jul. 23, 2015

(87) PCT Pub. No.: WO2014/119435
PCT Pub. Date: Aug. 7, 2014

(65) Prior Publication Data
US 2015/0369831 A1 Dec. 24, 2015

(30) Foreign Application Priority Data
Jan. 31, 2013 (JP) .................... 2013-016321

(51) Int. Cl.
*G01N 35/00* (2006.01)
*G01N 21/03* (2006.01)
(Continued)

(52) U.S. Cl.
CPC ...... *G01N 35/00732* (2013.01); *G01N 21/253* (2013.01); *G01N 21/274* (2013.01);
(Continued)

(58) Field of Classification Search
CPC ............... G01N 2015/1068; G01N 35/00623; G01N 35/00594; G01N 2035/009
See application file for complete search history.

(56) References Cited

FOREIGN PATENT DOCUMENTS

| JP | 64-451 A | 1/1989 |
|---|---|---|
| JP | 07-077492 A | 3/1995 |

(Continued)

OTHER PUBLICATIONS

Machine generated English translation for JP 2009-047545, published Mar. 5, 2009.*

(Continued)

*Primary Examiner* — P. Kathryn Wright
(74) *Attorney, Agent, or Firm* — Mattingly & Malur, PC

(57) ABSTRACT

An automatic analysis apparatus measures a concentration of an intended component in a biological sample, such as blood or urine, or determines whether such component is contained in the sample or not, and includes a function such that, with respect to the optical system, a part whose lifetime has ended is specified or the degree of deterioration of a part is detected to provide a user with the information. The automatic analyzer has a storage unit for storing a transmitted light distribution for a plurality of wavelengths detected by a receptor element for transmitted light which has passed through a substance to be measured, and a control unit for comparing a first, stored transmitted light distribution with a second transmitted light distribution acquired at the time of measurement to determine a deteriorating part from a plurality of parts based on the result of the comparison and output the result.

4 Claims, 7 Drawing Sheets

401. KNOWN TRANSMITTED LIGHT QUANTITY DISTRIBUTION
402. KNOWN INITIAL TRANSMITTED LIGHT QUANTITY DISTRIBUTION
403. KNOWN TRANSMITTED LIGHT QUANTITY DISTRIBUTION OBTAINED WHEN THE FILTER HAS DETERIORATED
404. KNOWN TRANSMITTED LIGHT QUANTITY DISTRIBUTION OBTAINED WHEN THE LAMP HAS DETERIORATED
405. TRANSMITTED LIGHT QUANTITY DISTRIBUTION OF THE APPARATUS
406. TRANSMITTED LIGHT QUANTITY DISTRIBUTION OF THE APPARATUS IMMEDIATELY AFTER BEING INSTALLED
407. LATEST TRANSMITTED LIGHT QUANTITY DISTRIBUTION MEASURED
408. WAVE-SHAPE CORRELATION OPERATOR
409. INFORMATION PROVIDING SCREEN FOR A USER

(51) Int. Cl.
  *G01N 21/31* (2006.01)
  *G01N 21/25* (2006.01)
  *G01N 21/27* (2006.01)
  *G01N 35/02* (2006.01)

(52) U.S. Cl.
  CPC ....... *G01N 21/314* (2013.01); *G01N 21/0332* (2013.01); *G01N 35/025* (2013.01); *G01N 2021/317* (2013.01); *G01N 2035/00356* (2013.01); *G01N 2201/12707* (2013.01); *G01N 2201/12723* (2013.01); *G01N 2201/12753* (2013.01)

(56) References Cited

FOREIGN PATENT DOCUMENTS

| | | |
|---|---|---|
| JP | 09-229939 A | 9/1997 |
| JP | 11-342123 A | 12/1999 |
| JP | 2004-251802 A | 9/2004 |
| JP | 200947545 A * | 3/2009 |
| JP | 2010-243222 A | 10/2010 |
| JP | 2011-117746 A | 6/2011 |
| WO | 88/06286 A1 | 8/1988 |

OTHER PUBLICATIONS

Machine generated English for JP 2004-251802, published Sep. 9, 2004.*
International Search Report of PCT JP2014/051172.
Extended European Search Report received in corresponding European Application No. 14746842.5 dated Sep. 23, 2016.

* cited by examiner

101. TRAVELING LINE
102. ROTOR
103. REAGENT DISC
104. REACTION DISC
105. INJECTION MECHANISM
106. STIRRING MECHANISM
107. SPECTROSCOPE
110. BIOLOGICAL SAMPLE CONTAINER
111. BIOLOGICAL SAMPLE RACK
112. REACTION CONTAINER
113. REAGENT CONTAINER
114. SHIELD PORTION
115. CONTROL UNIT

201. AUTOMATIC ANALYSIS APPARATUS
204. ANALYZER UNIT
206. REACTION LIQUID
208. REACTION CONTAINER
212. REACTION VESSEL
213. HEAT INSULATION MEDIUM
215. REACTION DISC
216. REACTION DISC MOTOR
217. LIGHT SOURCE
218. SPECTROSCOPE
220. OPTICAL FILTER

301. TRANSMITTED LIGHT
302. SPECTROSCOPE
303. LIGHT EMITTER
304. Log AMPLIFIER
305. LIGHT INTENSITY SIGNAL PROCESSING UNIT
307. AD CONVERTER
308. LIGHT QUANTITY DATA STORAGE UNIT
309. CPU

FIG. 4

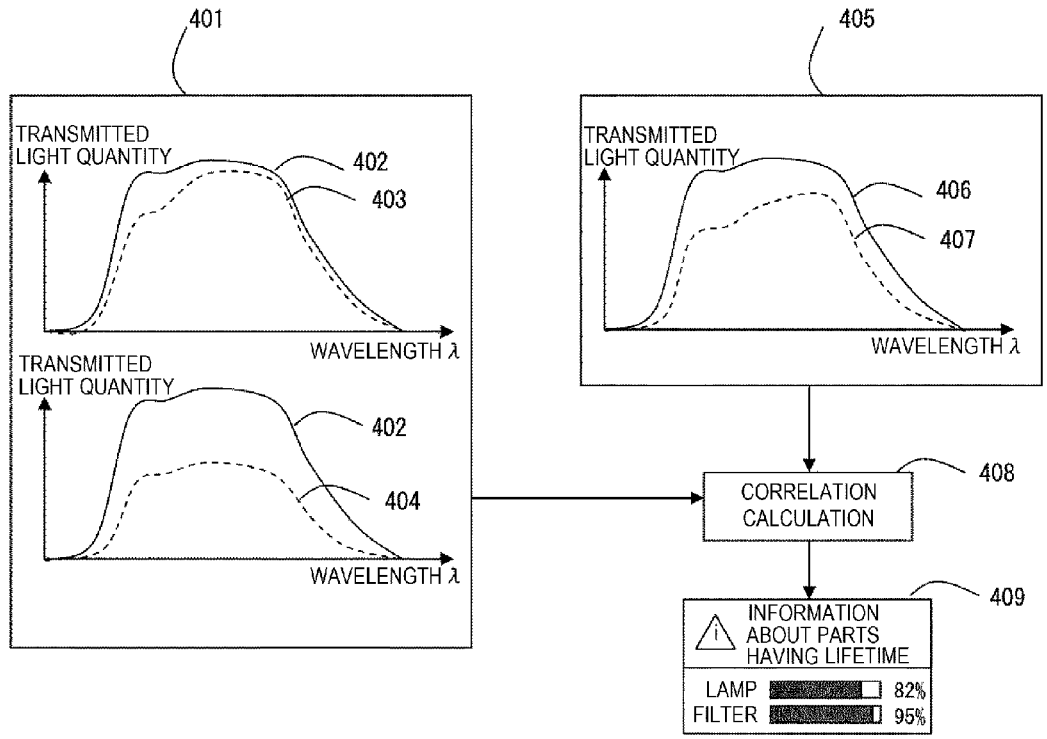

401. KNOWN TRANSMITTED LIGHT QUANTITY DISTRIBUTION
402. KNOWN INITIAL TRANSMITTED LIGHT QUANTITY DISTRIBUTION
403. KNOWN TRANSMITTED LIGHT QUANTITY DISTRIBUTION OBTAINED WHEN THE FILTER HAS DETERIORATED
404. KNOWN TRANSMITTED LIGHT QUANTITY DISTRIBUTION OBTAINED WHEN THE LAMP HAS DETERIORATED
405. TRANSMITTED LIGHT QUANTITY DISTRIBUTION OF THE APPARATUS
406. TRANSMITTED LIGHT QUANTITY DISTRIBUTION OF THE APPARATUS IMMEDIATELY AFTER BEING INSTALLED
407. LATEST TRANSMITTED LIGHT QUANTITY DISTRIBUTION MEASURED
408. WAVE-SHAPE CORRELATION OPERATOR
409. INFORMATION PROVIDING SCREEN FOR A USER

501. DATABASE PRELIMINARILY EXPERIMENTALLY DETERMINED AND STORED
502. REAL-TIME ACQUIRED DATA
503. REAL-TIME OPERATION CONTENTS
504. OPERATION RESULT EXAMPLE

FIG. 6

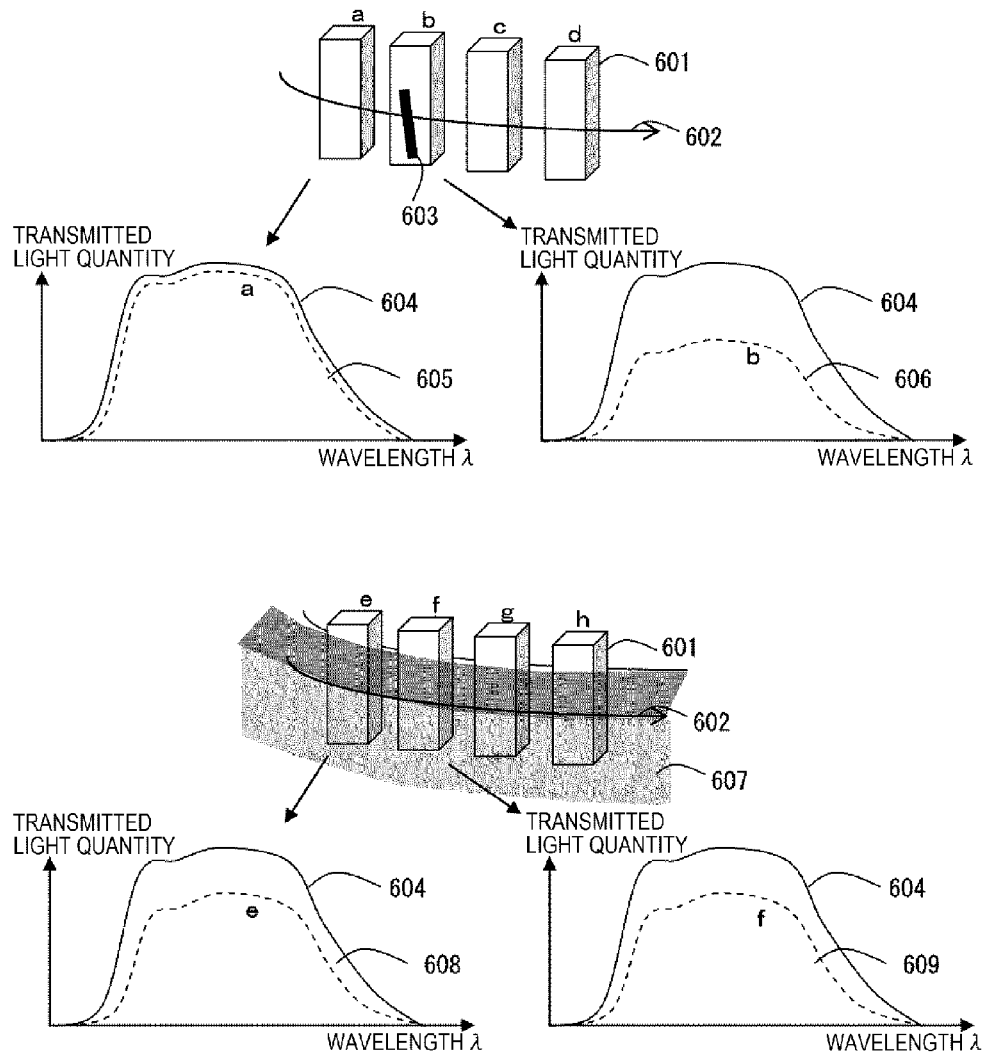

601. REACTION CONTAINER
602. OPTICAL AXIS OF A LAMP
603. PHYSICAL FLAW IN THE REACTION CONTAINER
604. INITIAL TRANSMITTED LIGHT QUANTITY DISTRIBUTION
605. TRANSMITTED LIGHT QUANTITY DISTRIBUTION OF A REACTION CONTAINER (a) HAVING NO FLAW
606. TRANSMITTED LIGHT QUANTITY DISTRIBUTION OF A REACTION CONTAINER (b) HAVING A FLAW
607. POLLUTED HEAT INSULATION MEDIUM
608. TRANSMITTED LIGHT QUANTITY DISTRIBUTION OF A REACTION CONTAINER (e)
609. TRANSMITTED LIGHT QUANTITY DISTRIBUTION OF A REACTION CONTAINER (f)

701. BASIC DATA ACQUISITION IN A SERIES OF APPARATUSES
702. INSTANTANEOUS DATA ACQUISITION IN EACH APPARATUS
703. DATA ACQUISITION AFTER THE CONDITION RENEWAL IN EACH APPARATUS

AUTOMATIC ANALYSIS APPARATUS

TECHNICAL FIELD

The present invention is directed to an automatic analysis apparatus for performing a qualitative or quantitative analysis for a biological sample, such as blood or urine, and relates to an automatic analysis apparatus having a system for measuring a quantity of light from a reaction container, wherein the reaction container is disposed between a light source and a spectroscopic detector.

BACKGROUND ART

An automatic analysis apparatus is used for measuring a concentration of an intended component in a biological sample, such as blood or urine, or knowing whether the intended component is contained in the sample or not. As compared to the measurement manually made by an inspection expert, the automatic analysis apparatus has a high analysis speed and high analysis accuracy (reproducibility), and therefore is spreading mainly through large hospitals and inspection laboratory centers.

In the automatic analysis apparatus, for measuring an absorbance, while rotating rotary reaction containers continuously arranged on the circumference, the optical axis is moved successively toward one reaction container to the next one to measure an absorbance. The apparatus has a light projection lamp for projecting a light against the rotary reaction containers, and a band transmission optical filter for preventing a light in the unnecessary wavelength band from arriving at the detector. These facilities are known to deteriorate in properties with the passage of time due to their own properties, and hence they are parts that need to be periodically replaced by other ones.

Conventionally, the inspection quality has been secured by surely conducting the periodic replacement of a part so as not to cause the deterioration of the part to adversely affect the performance of the apparatus.

As a technique for achieving the above object, PTL 1 discloses a technique in which a change of the photometric point absorbance is observed during the analysis to detect a lamp malfunction during the analysis.

Further, PTL 2 discloses a technique related to a method for determining the timing for the replacement of a light source lamp.

CITATION LIST

Patent Literature

PTL 1: JP-A-9-229939
PTL 2: JP-A-2011-117746

SUMMARY OF INVENTION

Technical Problem

In the technique described in PTL 1, the transition to a lamp malfunction is detected during the analysis by utilizing the data for the reaction process. By this method, a malfunction caused during the analysis can be detected; however, it is impossible to detect a lamp malfunction for a term as long as the duration of the use of the apparatus. Further, in the techniques of PTL 1 and PTL 2, the method of detecting a malfunction or deterioration of a lamp utilizing an absorbance at the wavelength used in the analysis is shown, but there is no disclosure about the detection of other malfunctions.

With respect to the deterioration of the optical system, there may be a case where it is difficult to specify that the deterioration is caused by the lamp or optical filter present on the optical axis of the photometer.

Further, there are some variations in the lifetimes of the respective parts including a lamp, and currently, a user is instructed to replace the part well before the time for each periodic replacement, and therefore replacement of the part is inevitably needed even though the life of the part has not ended. For this reason, there may be a case where a part is replaced before expiration of the duration of life of the part.

An object of the invention is to detect not only deterioration or malfunction of a lamp but also all the other deteriorations and malfunctions present on the optical axis of a photometer for a long term, using no detection of a malfunction by utilizing an absorbance at the wavelength predetermined in a certain analysis item.

Solution to Problem

For solving the above-mentioned problems, the construction of the present invention is as follows.

The invention is directed to an automatic analysis apparatus which has a storage unit for storing a transmitted light distribution for a plurality of wavelengths detected by a receptor element when measuring a transmitted light which has passed through a substance to be measured from a light source, and a control unit for comparing a first transmitted light distribution preliminarily stored in the storage unit with a second transmitted light distribution acquired at the time of measurement, wherein the control unit specifies a deteriorating part from a plurality of parts based on the result of the comparison and outputs the specified part.

The individual parts have different tendencies of the deterioration due to light wavelengths and therefore, by comparing a transmitted light distribution for a plurality of wavelengths obtained when a part has deteriorated with a transmitted light distribution acquired at the time of measurement, the deteriorating part can be specified from a plurality of parts. Further, by measuring tendencies of the reduction of the transmitted light quantity with the passage of time of the usage with respect to different wavelengths and comparing the tendencies between the wavelengths, malfunctions and deteriorations of a light source lamp and an optical filter are classified by each cause and information about this can be given to a user.

Advantage Effects of Invention

By the invention, a deteriorating part can be easily specified from a plurality of parts, making it possible to easily grasp the part to be replaced.

Further, by the invention, the degree of deterioration of each part can be output, and hence information about the replacement according to the actual degree of deterioration can be given to a user, so that the user can use the part until the duration of life of the part ends. Therefore, it is expected that the frequency of the replacement of parts can be reduced, improving the maintenance properties including maintenance cost reduction.

BRIEF DESCRIPTION OF DRAWINGS

FIG. 4 An example of the position of a reaction container and the transmitted light intensity.

FIG. 6 An example of a phenomenon in which detection of other malfunctions can be expected.

DESCRIPTION OF EMBODIMENTS

Hereinbelow, the present invention will be described in detail with reference to the following embodiment.

Figure 1:
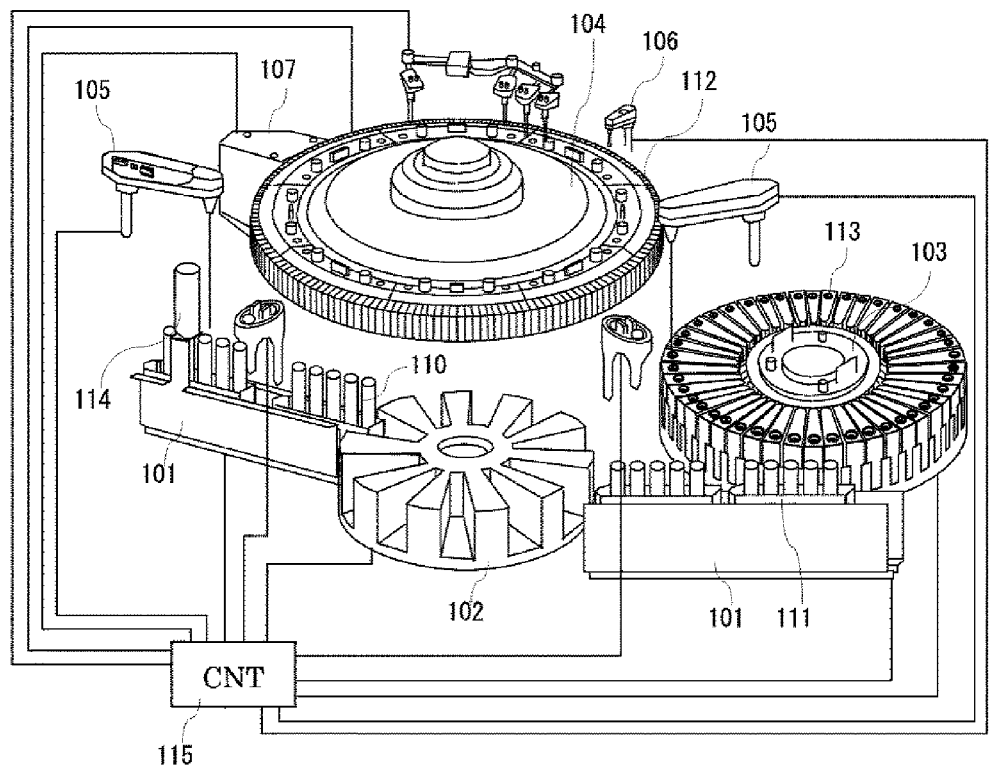
FIG. 1 A diagrammatic view of the construction of one embodiment of the automatic analysis apparatus of the invention.

FIG. 1 is a diagrammatic view of the construction of one embodiment of the automatic analysis apparatus of the invention.

The automatic analysis apparatus according to the present embodiment is constructed mainly from a traveling line (101), a reaction disc (104), a reagent disc (103), and a spectroscope (107).

A biological sample rack (111) on which biological sample containers (110) are laid is moved from the traveling line (101) to a rotor (102), and moved to a shield portion (114) which is the position for injection. Then, a biological sample necessary for the analysis is injected by an injection mechanism (105) into a reaction container (112) on the reaction disc (104). Further, a required reagent is injected from a reagent container (113) on the reagent disc (103) into the reaction container (112), and the resultant reaction liquid is mixed by a stirring mechanism (106).

With respect to the reaction liquid, an absorbance is measured by the spectroscope (107). These mechanisms are controlled by a control unit (115). The measured absorbance is stored in a storage unit contained in the control unit (115).

Figure 2:
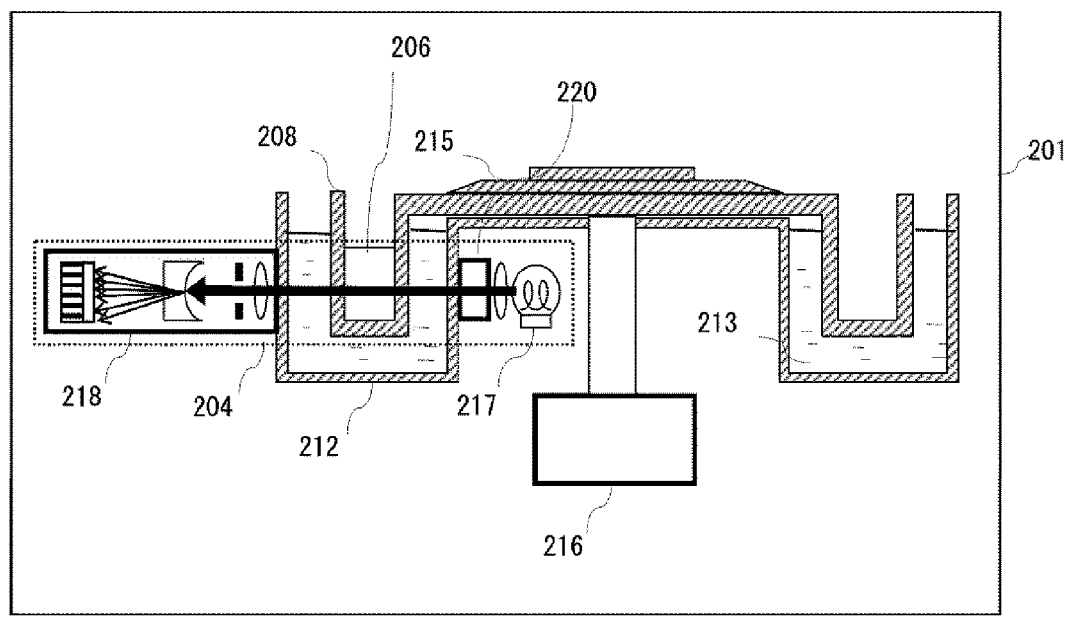
FIG. 2 A detail view of the light intensity measurement in the automatic analysis apparatus.

FIG. 2 is a detail view of the light intensity measurement in the automatic analysis apparatus of the invention.

In FIG. 2, in an automatic analysis apparatus (201), an analyzer unit (204) performs an analysis such that a light from a light source (217) is passed through a reaction liquid (206), which is formed by reacting a biological sample and a reagent in a reaction container (208) in the analyzer unit, to make a compositional analysis by a spectroscope (218).

The reaction container (208) in the analyzer unit (204) is immersed in a heat insulation medium (213), such as water, stored in a reaction vessel (212), and maintained at a constant temperature.

A plurality of the reaction containers (208) are disposed on a reaction disc (215), and rotated or moved together with the reaction disc (215) by controlling a reaction disc motor (216) by the control unit (115), so that the containers travel back and forth between the spectroscope (118) and the stirring mechanism (106) or the injection mechanism (105).

Figure 3:
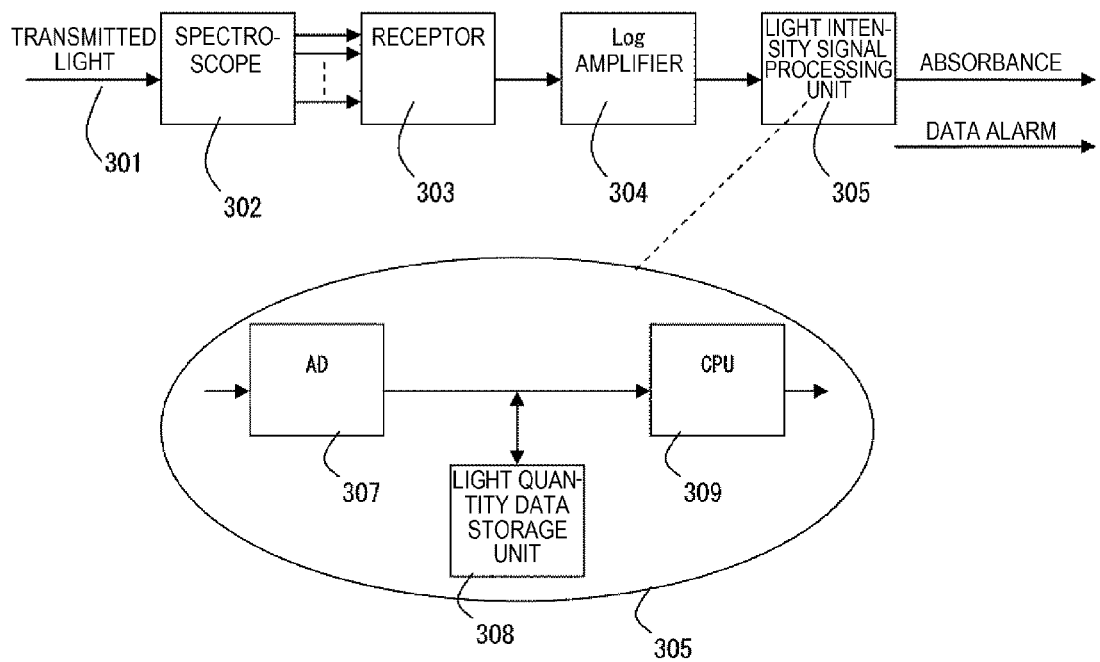
FIG. 3 A block diagram of the absorbance measurement and total wave-shape analysis.

FIG. 3 is an example of a block diagram of the light intensity measurement in the automatic analysis apparatus of the invention.

The photometer is constructed from a spectroscope (302), a receptor (303), a Log amplifier (304), and a light intensity signal processing unit (305).

The light intensity signal processing unit (305) is constructed from an AD converter (307), a light quantity data storage unit (308), and a CPU (309).

A transmitted light (301), which has passed through the reaction liquid from a light source lamp, is divided by the spectroscope (302) into individual wavelengths, and converted to a current according to the intensity of the light for each wavelength received by the receptor (303), and amplified by the Log amplifier (304) to a voltage signal such that a weak current signal can be easily handled, and subjected to processing, such as correction, in the light intensity signal processing unit (305) to determine a final transmitted light quantity.

In the light intensity signal processing unit (305), the amplified voltage signal is converted to a digital value, followed by data conversion in the CPU (309), to output an absorbance using two wavelengths among a plurality of wavelengths in a general analysis item.

Simultaneously, the voltage signal converted to a digital value is temporarily stored in the light quantity data storage unit (308). Data for light quantity with respect to a colorless and transparent liquid, such as pure water, measured immediately after installing the apparatus in a place where the apparatus is used, or immediately after replacing the part whose lifetime has ended is also stored in the light quantity data storage unit.

A data analysis is performed in the CPU (309) (hereinafter, referred to also as "control unit") based on the data temporarily stored, and the data is compared with the light quantity data previously measured with respect to a colorless and transparent liquid to specify a deteriorating part or calculate the degree of deterioration of a part for optical system.

With respect to the result of the calculation, the information can be provided with a user by means of a display device, such as a display. Further, when the data analysis detects the fact that the duration of life of a part is close to the end, for example, when the degree of deterioration becomes a predetermined degree, an alarm or the like can be output from the apparatus to provide information so as to urge a user or a field engineer to replace or clean the part.

FIG. 4 shows an example of the specification of a deteriorating part or the detection of deterioration of a part having a lifetime by a light quantity data analysis in the automatic analysis apparatus of the invention.

With respect to parts having a lifetime, such as an optical filter and a lamp, properties of the reduction of the transmitted light quantity against the wavelengths due to deterioration are preliminarily experimentally examined, and stored as a database in the form of a known transmitted light quantity distribution (403) obtained when the filter has deteriorated and a known transmitted light quantity distribution (404) obtained when the lamp has deteriorated.

A known transmitted light quantity distribution (401) is preliminarily stored in the light quantity data storage unit (308) in the apparatus. Further, as initial data at the time of the installation of the apparatus in a place where the apparatus is used or the replacement of a part, a transmitted light quantity distribution (406) of the apparatus immediately after being installed is also stored in the light quantity data storage unit (308).

The known transmitted light quantity distribution (403) obtained when the filter has deteriorated tends to be different from a known initial transmitted light quantity distribution (402) in respect of the properties of the reduction of the transmitted light quantity against the wavelengths. On the other hand, the known transmitted light quantity distribution (404) obtained when the lamp has deteriorated has a tendency that the properties of the reduction of the transmitted light quantity against the wavelengths are uniform irrespective of the wavelengths. For this reason, by analyzing the tendency of the reduction of the transmitted light from a transmitted light quantity distribution (407) measured in the latest measurement by the apparatus and the transmitted light quantity distribution (406) of the apparatus immediately after being installed, apart of the cause of deterioration can be specified and classified.

With respect to a transmitted light quantity distribution (405) of the apparatus and the known transmitted light quantity distribution (401), by making an analysis using a wave-shape correlation operator (408), information about the specification of the deteriorating part or the degree of lifetime as information of the parts having a lifetime can be provided on an information providing screen (409) for a user.

Further, a user can grasp in advance the degree of preparation for the parts having a lifetime.

Thus, from an initial transmitted light quantity distribution and a transmitted light quantity distribution obtained when the part has deteriorated with respect to each of the parts, and a transmitted light quantity distribution of the apparatus immediately after being installed, the control unit calculates a correlation between the distributions, and the control unit can output the degree of deterioration of each of the parts based on the transmitted light distribution at the time of measurement and the calculated correlation.

The parts are parts disposed on an optical axis of the light source, and an optical filter, a lamp, the below-described reaction container containing therein a substance to be measured, and a heat insulation medium for keeping the reaction container warm can be applied to the parts, and a combination of other parts and a combination of the above parts can also be applied to the parts.

Figure 5:
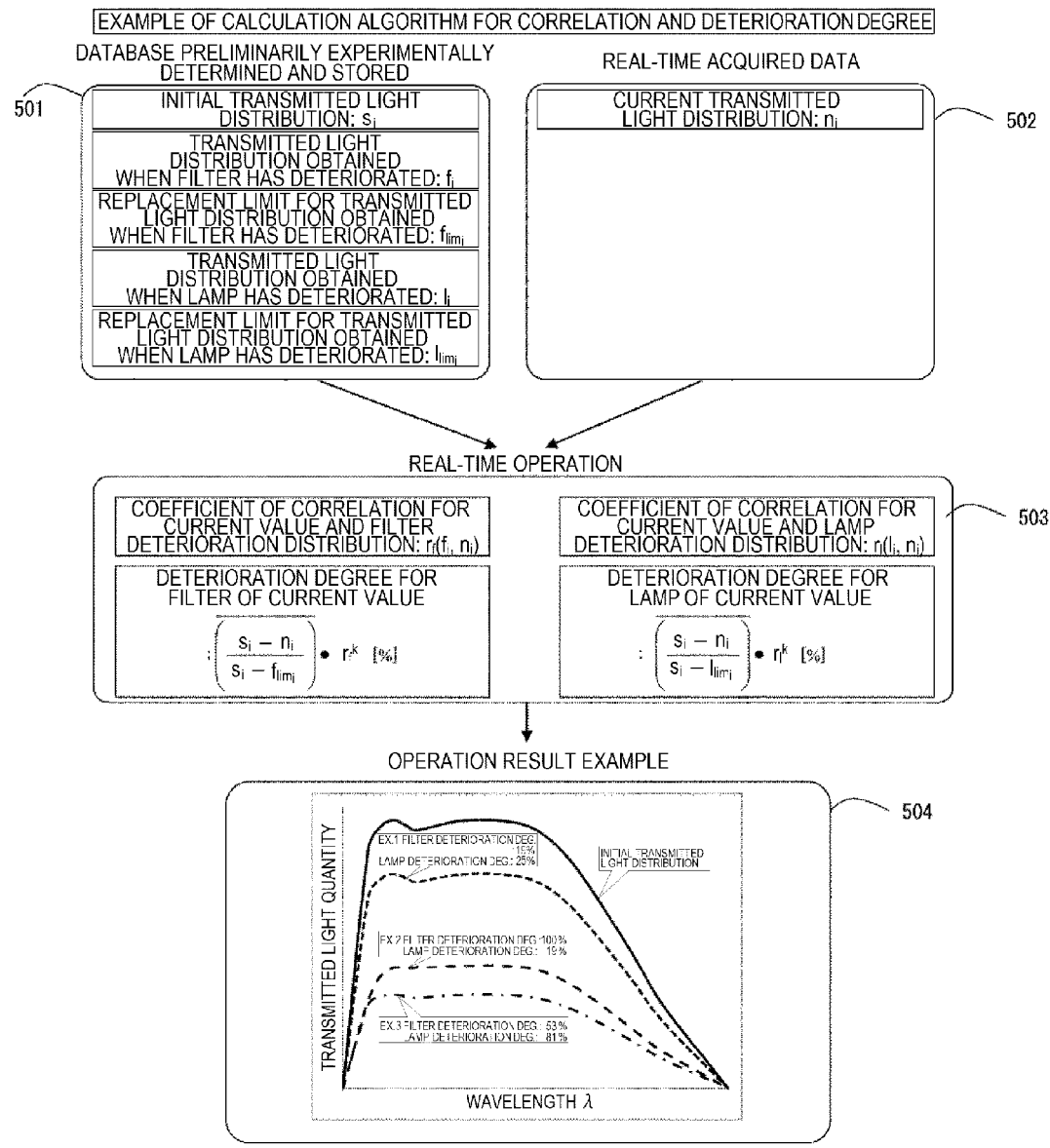
FIG. 5 An example of calculation algorithm for the correlation and deterioration degree.

FIG. 5 shows an example of calculation algorithm for the correlation and deterioration degree in the automatic analysis apparatus of the invention.

As an example, an operation concerning the deterioration of an optical filter and a lamp is described.

As a database (501) which has been preliminarily experimentally determined and stored, the apparatus has an initial transmitted light distribution, transmitted light distributions obtained respectively when the optical filter and lamp have deteriorated, and each transmitted light distribution at the limit in which the replacement is recommended by the manufacturer.

Further, the individual automatic analysis apparatus has a current transmitted light distribution as a real-time acquired data (502).

From the above data, as shown in real-time operation contents (503), an operation for a correlation between the current transmitted light distribution and the transmitted light distribution obtained when each part has deteriorated is conducted, and further an operation for the current deterioration degree of each part is conducted.

Consequently, an example of the calculation of the degree of deterioration of each part made under three current transmitted light distribution conditions is shown as an operation result example (504).

FIG. 6 shows an example of a phenomenon in which detection of other malfunctions can be expected in the automatic analysis apparatus of the invention.

With respect to other detectable information, the deterioration of a reaction container (601) and pollution of a heat insulation medium (607) can be expected to be detected.

When a physical flaw (603) is caused in the reaction container (601), a transmitted light quantity distribution (606) of a reaction container (b) having a flaw is likely to be lowered in the transmitted light quantity, as compared to a transmitted light quantity distribution (605) of a reaction container (a) having no flaw. In the deterioration of a lamp or a filter described above with reference to FIG. 4, with respect to the transmitted light quantity distribution for the light which has passed through all the reaction containers passing an optical axis (602) of the lamp, similar properties of the reduction of the transmitted light quantity are exhibited. However, in the case of a malfunction of a single reaction container, properties of the reduction of the transmitted light quantity characteristic of the reaction container are exhibited, and therefore, by comparing the transmitted light quantity distributions of the reaction containers adjacent to each other as measured at the same point in time, a malfunction in respect of the individual reaction containers can be detected.

Further, when a heat insulation medium is polluted due to rotting or the like, the photometer is lowered in the dynamic range, leading to a lowering of the analysis accuracy. When comparing the transmitted light quantities using the polluted heat insulation medium (607), a transmitted light quantity distribution (608) of a reaction container (e) and a transmitted light quantity distribution (609) of an adjacent reaction container (f) exhibit similar properties of the reduction of the light quantity, as compared to an initial transmitted light quantity distribution (604), and therefore can be distinguished from the above-mentioned detection of a malfunction of the individual reaction containers.

Utilizing such properties, the deteriorating part can be specified or the degree of deterioration can be output.

Figure 7:
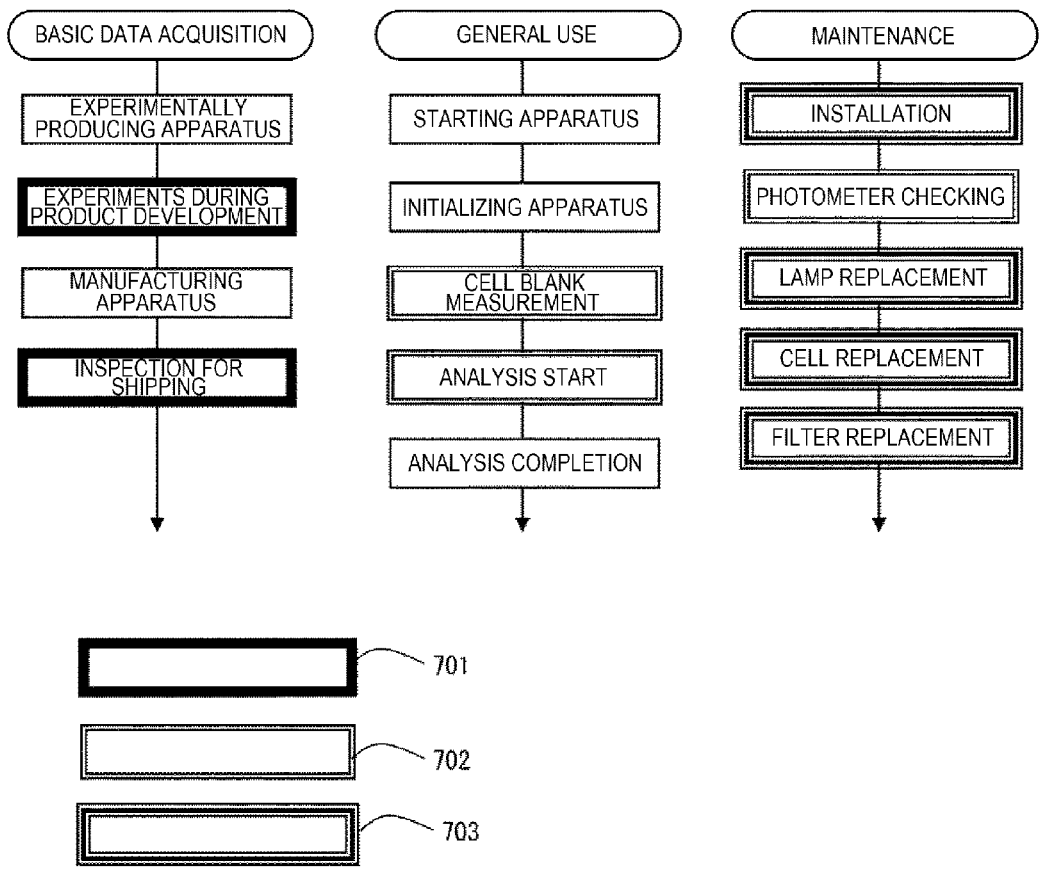
FIG. 7 An example of the data acquisition timing.

FIG. 7 shows an example of the data acquisition timing in the automatic analysis apparatus of the invention.

A basic data acquisition in a series of apparatuses (701) acquires data in order to establish a database for the parts which are normal and malfunction as general properties of a series of apparatuses. An instantaneous data acquisition in each apparatus (702) is a data acquisition for checking the current degree of lifetime or whether a malfunction occurs or not. A data acquisition after the condition renewal in each apparatus (703) acquires a transmitted light distribution characteristic of the apparatus, and, after completion of the installation of the apparatus, data to be stored as an initial transmitted light quantity distribution of the apparatus is acquired. Further, also when the condition of the apparatus is changed by replacement of the part whose lifetime has ended, or the like, data is acquired, and the stored initial transmitted light distribution data is replaced by the acquired data.

REFERENCE SIGN LIST

101. Traveling line
102. Rotor
103. Reagent disc
104. Reaction disc
105. Injection mechanism
106. Stirring mechanism
107. Spectroscope
110. Biological sample container
111. Biological sample rack
112. Reaction container
113. Reagent container
114. Shield portion
115. Control unit
201. Automatic analysis apparatus
204. Analyzer unit
206. Reaction liquid
208. Reaction container
212. Reaction vessel
213. Heat insulation medium 215. Reaction disc
216. Reaction disc motor
217. Light source
218. Spectroscope
220. Optical filter
301. Transmitted light
302. Spectroscope
303. Light emitter
304. Log amplifier
305. Light intensity signal processing unit
307. AD Converter
308. Light quantity data storage unit
309. CPU
401. Known transmitted light quantity distribution
402. Known initial transmitted light quantity distribution
403. Known transmitted light quantity distribution obtained when the filter has deteriorated
404. Known transmitted light quantity distribution obtained when the lamp has deteriorated
405. Transmitted light quantity distribution of the apparatus
406. Transmitted light quantity distribution of the apparatus immediately after being installed
407. Latest transmitted light quantity distribution measured
408. Wave-shape correlation operator
409. Information providing screen for a user
501. Database preliminarily experimentally determined and stored
502. Real-time acquired data
503. Real-time operation contents
504. Operation result example
601. Reaction container
602. Optical axis of a lamp
603. Physical flaw in the reaction container
604. Initial transmitted light quantity distribution
605. Transmitted light quantity distribution of a reaction container (a) having no flaw
606. Transmitted light quantity distribution of a reaction container (b) having a flaw
607. Polluted heat insulation medium
608. Transmitted light quantity distribution of a reaction container (e)
609. Transmitted light quantity distribution of a reaction container (f)
701. Basic data acquisition in a series of apparatuses
702. Instantaneous data acquisition in each apparatus
703. Data acquisition after the condition renewal in each apparatus

The invention claimed is:

1. An automatic analysis apparatus, comprising:
a reaction disk holding a plurality of reaction containers, one or more of the reaction containers holding a sample to be analyzed;
a reaction disk motor configured to drive the reaction disk;
a display;
an analyzer unit including a light source, an optical filter, a spectroscope, and a receptor element configured to measure light transmitted from the light source through a reaction container and a sample within the reaction container; and
a control unit connected to the reaction disk motor, the analyzer unit, and the display, that includes a data storage unit,
wherein the data storage unit stores:
an initial transmitted light quantity distribution of each of the light source and the optical filter,
a known transmitted light quantity distribution of each of the light source and the optical filter when the light source and the optical filter, respectively, have experimentally been determined to be deteriorated, and
an initial transmitted light quantity distribution using light transmitted from the light source and passing through the optical filter,
wherein the control unit is programmed to:
cause the light source to emit light;
obtain a measured transmitted light quantity distribution for a plurality of wavelengths detected by the receptor element when measuring the light emitted from the light source that is transmitted through the reaction container and through the sample to the receptor element via the spectroscope,
store the measured transmitted light quantity distribution for the plurality of wavelengths,
determine a first correlation between the initial transmitted light quantity distribution of the light source, the known transmitted light quantity distribution of the light source, and the initial transmitted light quantity distribution using light transmitted from the light source and passing through the optical filter,
determine a second correlation between the initial transmitted light quantity distribution of the optical filter, the known transmitted light quantity distribution of the optical filter, and the initial transmitted light quantity distribution using light transmitted from the light source and passing through the optical filter,
determine a degree of deterioration for the light source and the optical filter based on the first correlation and the measured transmitted light distribution for the plurality of wavelengths and the second correlation and the measured transmitted light distribution for the plurality of wavelengths, respectively, and
cause the display to display an indication of the degree of deterioration for each of the light source and the optical filter.

2. The automatic analysis apparatus according to claim 1, wherein the control unit is programmed to:
cause the reaction disk motor to drive at least two of the one or more reaction containers holding a sample to be analyzed into the analyzing unit,
for each reaction container driven into the analyzing unit, cause the light source and the receptor element to obtain the measured transmitted light quantity distribution and store the obtained measured transmitted light quantity distributions,
compare the measured transmitted light quantity distributions for each of the at least two reaction containers and determine based on the comparison whether a reaction container has been deteriorated, and
cause the display to display an indication that the reaction container is deteriorated if the reaction container is determined to be deteriorated.

3. The automatic analysis apparatus according to claim 2, further comprising: a heat insulation medium for keeping the plurality of reaction containers at a predetermined temperature.

4. The automatic analysis apparatus according to claim 1, wherein the control unit is programmed to:
when the degree of deterioration of any of the light source and the optical filter becomes a predetermined degree, cause the display to display an alarm corresponding to the light source or the optical filter.

* * * * *